United States Patent [19]
Mahurkar

[11] Patent Number: 6,117,112
[45] Date of Patent: Sep. 12, 2000

[54] SINGLE-USE SAFETY SYRINGE

[76] Inventor: Sakharam D. Mahurkar, 6171 N. Sheridan Rd., Suite 1112, Chicago, Ill. 60660

[21] Appl. No.: 08/972,548

[22] Filed: Nov. 18, 1997

[51] Int. Cl.[7] ...................................................... A61M 5/32
[52] U.S. Cl. ........................................... 604/194; 604/110
[58] Field of Search ...................................... 604/110, 194, 604/195, 196, 198, 263, 523, 246, 247, 254

[56] References Cited

U.S. PATENT DOCUMENTS

| | | |
|---|---|---|
| D. 298,352 | 11/1988 | Raines . |
| 2,888,923 | 6/1959 | Reis . |
| 2,925,083 | 1/1960 | Craig . |
| 3,610,240 | 10/1971 | Harautuneian . |
| 3,658,061 | 4/1972 | Hall . |
| 4,068,659 | 1/1978 | Moorehead . |
| 4,233,982 | 11/1980 | Bauer et al. . |
| 4,245,635 | 1/1981 | Kontos . |
| 4,261,357 | 4/1981 | Kontos . |
| 4,274,408 | 6/1981 | Nimrod . |
| 4,417,886 | 11/1983 | Franhouser et al. . |
| 4,424,833 | 1/1984 | Spector et al. . |
| 4,425,120 | 1/1984 | Sampson et al. . |
| 4,468,224 | 8/1984 | Enzmann et al. . |
| 4,529,399 | 7/1985 | Groshong et al. . |
| 4,631,057 | 12/1986 | Mitchell . |
| 4,659,330 | 4/1987 | Nelson et al. . |
| 4,664,654 | 5/1987 | Strauss . |
| 4,666,435 | 5/1987 | Braginetz . |
| 4,693,708 | 9/1987 | Wanderer et al. . |
| 4,702,738 | 10/1987 | Spencer . |
| 4,710,170 | 12/1987 | Haber et al. . |
| 4,731,059 | 3/1988 | Wanderer et al. . |
| 4,731,068 | 3/1988 | Hesse . |
| 4,732,162 | 3/1988 | Martell . |
| 4,735,617 | 4/1988 | Nelson et al. . |

(List continued on next page.)

FOREIGN PATENT DOCUMENTS

| | | |
|---|---|---|
| 0 360 313 | 3/1990 | European Pat. Off. . |
| 0 754 469 A2 | 6/1996 | European Pat. Off. . |
| 2004771 | 11/1969 | France . |
| 24 15 196 | 10/1975 | Germany . |
| 25 07 119 | 9/1976 | Germany . |
| 30 42 229 | 5/1982 | Germany . |
| 38 33 138 | 4/1990 | Germany . |
| WO84/01510 | 4/1984 | WIPO . |
| WO90/15634 | 12/1990 | WIPO . |
| WO93/00950 | 1/1993 | WIPO . |
| WO 97/06841 | 2/1997 | WIPO . |

OTHER PUBLICATIONS

"Health Care" by Helene Cooper, Wall Street Journal (Nov. 25, 1992).

The G.M.P. Letter (May 1992).

(List continued on next page.)

*Primary Examiner*—Mark O. Polutta
*Assistant Examiner*—Jeremy Thissell
*Attorney, Agent, or Firm*—Stephen G. Rudisill

[57] ABSTRACT

A single-use safety syringe assembly comprises an elongated, generally cylindrical barrel which forms a hollow nozzle located at the distal end of the barrel and which opens into the interior of the barrel. A plunger is slidably mounted in the barrel and forms a longitudinal cavity. A needle holder carries a hollow needle on the distal end, and the needle holder is slidably mounted in the longitudinal cavity of the plunger. The needle holder includes a lateral arm which extends between the plunger cavity and the barrel. A spiral guide slot through a wall of the barrel extends along a proximal end portion of the barrel for engaging the lateral arm of the needle holder and retracting the needle holder within the barrel in response to relative rotational movement between the barrel and the needle holder. A pair of longitudinal ribs strengthen the proximal end portion of the barrel. A locking element for releasably locking the needle holder lateral arm at a distal end of the spiral guide slot is slidably mounted on a track formed on one of the ribs. An OTN catheter may also be employed in combination with the syringe assembly.

35 Claims, 12 Drawing Sheets

U.S. PATENT DOCUMENTS

| | | |
|---|---|---|
| 4,735,618 | 4/1988 | Hagen . |
| 4,742,910 | 5/1988 | Staebler . |
| 4,746,017 | 5/1988 | Howard et al. . |
| 4,747,831 | 5/1988 | Kulli . |
| 4,747,835 | 5/1988 | Sandhaus . |
| 4,747,836 | 5/1988 | Luther . |
| 4,752,290 | 6/1988 | Schramm . |
| 4,762,516 | 8/1988 | Luther et al. . |
| 4,767,412 | 8/1988 | Hymanson . |
| 4,767,413 | 8/1988 | Haber et al. . |
| 4,778,453 | 10/1988 | Lopez . |
| 4,782,841 | 11/1988 | Lopez . |
| 4,790,822 | 12/1988 | Haining . |
| 4,799,926 | 1/1989 | Haber . |
| 4,801,295 | 1/1989 | Spencer . |
| 4,808,169 | 2/1989 | Haber et al. . |
| 4,813,426 | 3/1989 | Haber et al. . |
| 4,813,938 | 3/1989 | Raulerson . |
| 4,816,024 | 3/1989 | Sitar et al. . |
| 4,819,659 | 4/1989 | Sitar . |
| 4,826,488 | 5/1989 | Nelson et al. . |
| 4,826,489 | 5/1989 | Haber et al. . |
| 4,826,491 | 5/1989 | Schramm . |
| 4,828,107 | 5/1989 | Spencer . |
| 4,828,548 | 5/1989 | Walter . |
| 4,832,696 | 5/1989 | Luther et al. . |
| 4,834,717 | 5/1989 | Haber et al. . |
| 4,838,871 | 6/1989 | Luther . |
| 4,842,591 | 6/1989 | Luther . |
| 4,846,811 | 7/1989 | Vanderhoof . |
| 4,850,961 | 7/1989 | Wanderer et al. . |
| 4,850,976 | 7/1989 | Heinrich et al. . |
| 4,852,584 | 8/1989 | Selby . |
| 4,860,742 | 8/1989 | Park et al. . |
| 4,863,435 | 9/1989 | Sturman et al. . |
| 4,863,436 | 9/1989 | Glick . |
| 4,872,552 | 10/1989 | Unger . |
| 4,874,384 | 10/1989 | Nunez . |
| 4,883,469 | 11/1989 | Glazier . |
| 4,887,998 | 12/1989 | Martin et al. . |
| 4,892,525 | 1/1990 | Hermann, Jr. et al. . |
| 4,894,055 | 1/1990 | Sudnak . |
| 4,897,083 | 1/1990 | Martell . |
| 4,898,588 | 2/1990 | Roberts . |
| 4,900,311 | 2/1990 | Stern et al. . |
| 4,903,832 | 2/1990 | Stewart . |
| 4,906,235 | 3/1990 | Roberts . |
| 4,909,794 | 3/1990 | Haber et al. . |
| 4,911,693 | 3/1990 | Paris . |
| 4,915,696 | 4/1990 | Feimer . |
| 4,915,697 | 4/1990 | DuPont . |
| 4,917,673 | 4/1990 | Coplin . |
| 4,919,656 | 4/1990 | Bracker et al. . |
| 4,927,019 | 5/1990 | Haber et al. . |
| 4,927,417 | 5/1990 | Moncada et al. . |
| 4,928,824 | 5/1990 | Barasch . |
| 4,929,241 | 5/1990 | Kulli . |
| 4,931,040 | 6/1990 | Haber et al. . |
| 4,931,048 | 6/1990 | Lopez . |
| 4,932,940 | 6/1990 | Walker et al. . |
| 4,932,946 | 6/1990 | Shields . |
| 4,935,015 | 6/1990 | Hall . |
| 4,944,723 | 7/1990 | Haber et al. . |
| 4,944,728 | 7/1990 | Carrell et al. . |
| 4,944,731 | 7/1990 | Cole . |
| 4,946,447 | 8/1990 | Hardcastle et al. . |
| 4,950,241 | 8/1990 | Ranford . |
| 4,950,252 | 8/1990 | Luther et al. . |
| 4,958,622 | 9/1990 | Selenke . |
| 4,964,854 | 10/1990 | Luther . |
| 4,973,316 | 11/1990 | Dysarz . |
| 4,976,702 | 12/1990 | Andrews et al. . |
| 4,986,813 | 1/1991 | Blake, III et al. . |
| 4,986,819 | 1/1991 | Sobel . |
| 4,988,339 | 1/1991 | Vadher . |
| 4,994,042 | 2/1991 | Vadher . |
| 4,994,044 | 2/1991 | LoDuca . |
| 4,997,422 | 3/1991 | Chow et al. . |
| 5,000,167 | 3/1991 | Sunderland . |
| 5,002,536 | 3/1991 | Thompson et al. . |
| 5,013,304 | 5/1991 | Russell et al. . |
| 5,015,241 | 5/1991 | Feimer . |
| 5,019,045 | 5/1991 | Lee . |
| 5,019,051 | 5/1991 | Hake . |
| 5,024,326 | 6/1991 | Sandel et al. . |
| 5,024,660 | 6/1991 | McNaughton . |
| 5,026,345 | 6/1991 | Teringo . |
| 5,026,354 | 6/1991 | Kocses . |
| 5,030,209 | 7/1991 | Wanderer et al. . |
| 5,030,212 | 7/1991 | Rose . |
| 5,037,400 | 8/1991 | Curry . |
| 5,037,401 | 8/1991 | DeCamp . |
| 5,045,062 | 9/1991 | Henson . |
| 5,046,508 | 9/1991 | Weissler . |
| 5,049,136 | 9/1991 | Johnson . |
| 5,051,109 | 9/1991 | Simon . |
| 5,053,017 | 10/1991 | Chamuel . |
| 5,057,088 | 10/1991 | Narayanan et al. . |
| 5,057,089 | 10/1991 | Greco . |
| 5,059,180 | 10/1991 | McLees . |
| 5,061,249 | 10/1991 | Campbell . |
| 5,066,279 | 11/1991 | Russell . |
| 5,066,281 | 11/1991 | Stevenson-Michener . |
| 5,067,942 | 11/1991 | Jaffe et al. . |
| 5,067,944 | 11/1991 | Nichols . |
| 5,067,946 | 11/1991 | Zhadanov . |
| 5,067,949 | 11/1991 | Freundlich et al. . |
| 5,069,669 | 12/1991 | Kole . |
| 5,078,693 | 1/1992 | Shine . |
| 5,084,019 | 1/1992 | Gartz . |
| 5,086,780 | 2/1992 | Schmitt . |
| 5,088,987 | 2/1992 | Noonan, Jr. . |
| 5,088,988 | 2/1992 | Talonn et al. . |
| 5,092,853 | 3/1992 | Couvertier, II . |
| 5,098,394 | 3/1992 | Luther . |
| 5,098,402 | 3/1992 | Davis . |
| 5,098,405 | 3/1992 | Peterson et al. ........................ 604/247 |
| 5,106,379 | 4/1992 | Leap . |
| 5,106,380 | 4/1992 | Lobello . |
| 5,108,378 | 4/1992 | Firth et al. . |
| 5,112,307 | 5/1992 | Haber et al. . |
| 5,112,315 | 5/1992 | Gloyer et al. . |
| 5,114,404 | 5/1992 | Paxton et al. . |
| 5,116,325 | 5/1992 | Paterson . |
| 5,120,309 | 6/1992 | Watts . |
| 5,122,118 | 6/1992 | Haber et al. . |
| 5,125,898 | 6/1992 | Kaufhold, Jr. et al. . |
| 5,127,910 | 7/1992 | Talonn et al. . |
| 5,135,504 | 8/1992 | McLees . |
| 5,135,505 | 8/1992 | Kaufman . |
| 5,147,326 | 9/1992 | Talonn et al. . |
| 5,160,326 | 11/1992 | Talonn et al. . |
| 5,163,908 | 11/1992 | Lambert . |
| 5,163,917 | 11/1992 | Huefner et al. . |
| 5,171,300 | 12/1992 | Blake, III et al. . |
| 5,171,303 | 12/1992 | DeCamp . |
| 5,176,640 | 1/1993 | Nacci et al. . |
| 5,176,655 | 1/1993 | McCormick et al. . |
| 5,181,524 | 1/1993 | Wanderer et al. . |
| 5,183,468 | 2/1993 | McLees . |
| 5,188,119 | 2/1993 | Sunderland . |
| 5,188,611 | 2/1993 | Orgain . |

| | | |
|---|---|---|
| 5,188,613 | 2/1993 | Shaw . |
| 5,190,526 | 3/1993 | Murray et al. . |
| 5,190,532 | 3/1993 | Yu . |
| 5,195,973 | 3/1993 | Novick . |
| 5,195,975 | 3/1993 | Castagna . |
| 5,195,982 | 3/1993 | Hoenig . |
| 5,195,983 | 3/1993 | Boese . |
| 5,195,992 | 3/1993 | Dudar et al. . |
| 5,195,993 | 3/1993 | Gianakos . |
| 5,197,953 | 3/1993 | Colonna . |
| 5,197,954 | 3/1993 | Cameron . |
| 5,201,718 | 4/1993 | Whisson . |
| 5,215,524 | 6/1993 | Vallelunga et al. . |
| 5,215,525 | 6/1993 | Sturman . |
| 5,215,528 | 6/1993 | Purdy et al. . |
| 5,215,529 | 6/1993 | Fields et al. . |
| 5,215,533 | 6/1993 | Robb . |
| 5,215,534 | 6/1993 | DeHarde et al. . |
| 5,215,535 | 6/1993 | Gettig et al. . |
| 5,217,436 | 6/1993 | Lampropoulous . |
| 5,217,437 | 6/1993 | Farkas . |
| 5,218,965 | 6/1993 | Ring .................................. 600/486 |
| 5,219,333 | 6/1993 | Sagstetter et al. . |
| 5,219,338 | 6/1993 | Haworth . |
| 5,221,262 | 6/1993 | Kite . |
| 5,222,942 | 6/1993 | Bader . |
| 5,222,943 | 6/1993 | Mazzara . |
| 5,222,944 | 6/1993 | Harris . |
| 5,222,945 | 6/1993 | Basdnight . |
| 5,222,947 | 6/1993 | D'Amico .................................. 604/198 |
| 5,338,311 | 8/1994 | Mahurkar . |
| 5,643,222 | 7/1997 | Mahurkar .................................. 604/195 |

OTHER PUBLICATIONS

Devices & Diagnostics Letter, vol. 19, No. 19 (May 8, 1992).

FDA Medical Bulletin, vol. 22, No. 2 (Sep. 22, 1992).

"Safer Syringes Boost Molder Opportunities" by Carl Kirkland, Plastic World, vol. 51/No. 8, pp. 20–24, (Aug. 1993).

"Ultrasonics Get Medical Seal Of Approval" by Marcie Moskowitz, Plastic World, vol. 51/No. 8, pp. 26–28, (Aug. 1993).

Brochure for Arrow® Ravlerson Syringe.

Brochure for Syringes by Becton Dickinson of Franklin Lakes, New Jersey (1992).

Devices & Diagnostics Letter, p. 2 (Aug. 21, 1992).

Chiarello, Linda A., Reducing Needlestick Injuries among Health Care Workers: Aids Clinical Care Oct 1993 V.5 No. 10 Mass. Medical Society.

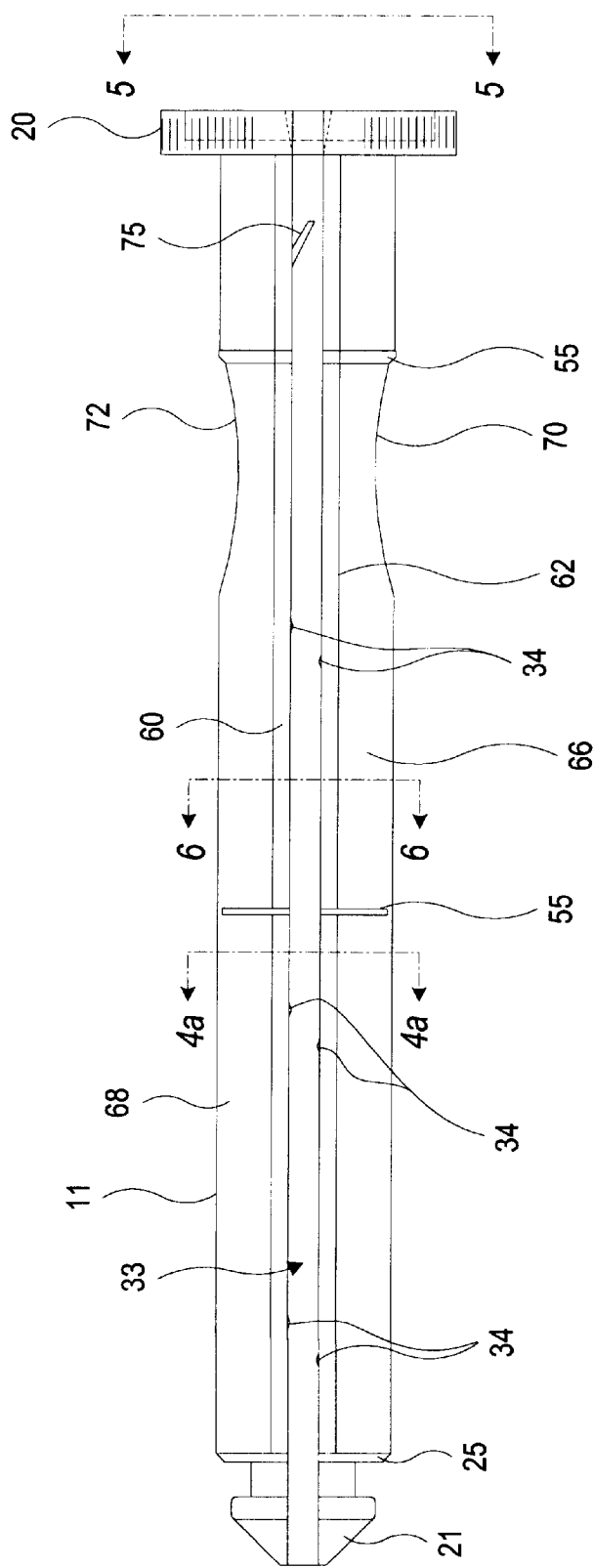
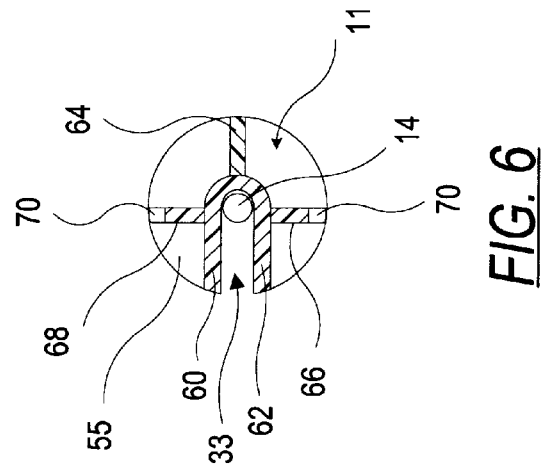
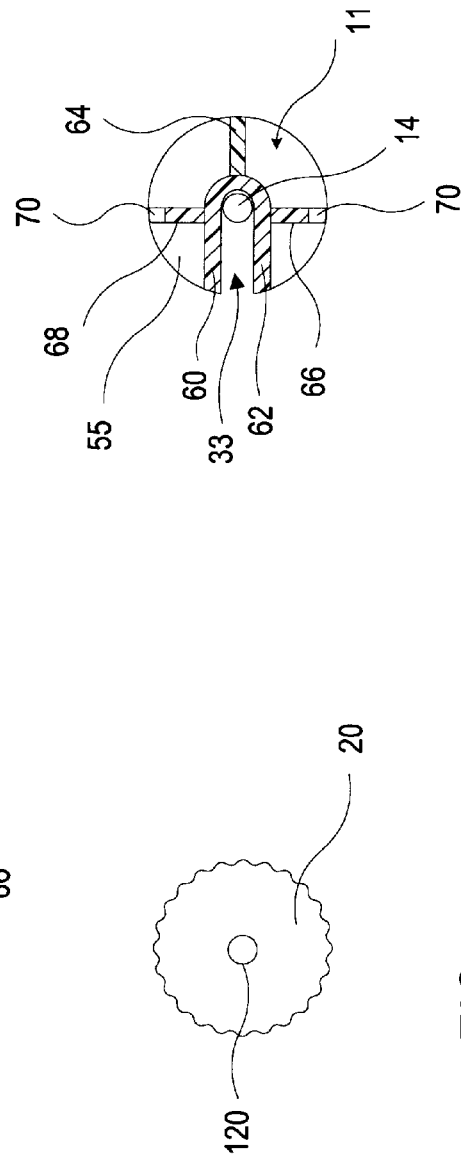
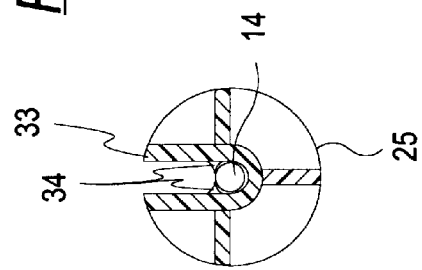

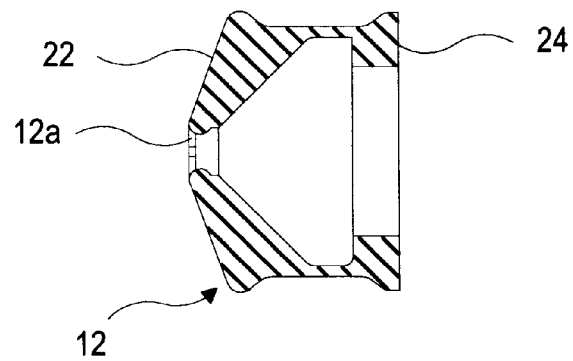
*FIG. 7*
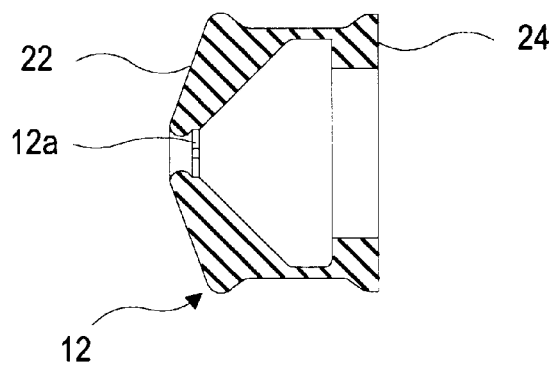 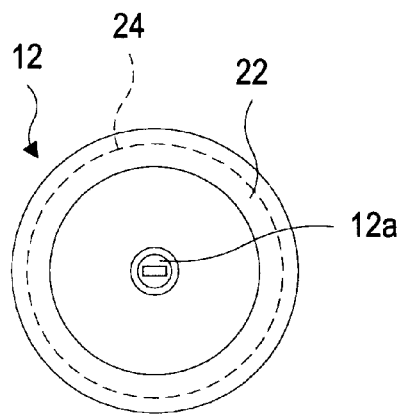
*FIG. 8*      *FIG. 9*

SINGLE-USE SAFETY SYRINGE

FIELD OF THE INVENTION

The present invention generally relates to hypodermic needles. In particular, the present invention relates to a syringe assembly which conceals the sharp point of the hypodermic needle following use.

BACKGROUND OF THE INVENTION

A hypodermic needle has many applications in modern medicine. One application is to fit the hypodermic needle onto a syringe and to then insert the needle into a person's body for intra-muscular, subcutaneous, or intravenous injection of medications. Another application of the hypodermic needle is to coaxially mount a catheter over a hypodermic needle and to puncture a vein of a person's body with the needle. Following needle puncture, the over-the-needle ("OTN") catheter is advanced into the vein, the needle is removed, and the catheter is connected to an intravenous line for fluid infusions into the vein.

A hypodermic needle entering into a patient's body is invariably contaminated by the patient's blood and body fluids. Following use of the needle, the needle presents a risk to physicians, nurses, and other health care personnel because the needle might transmit an infection or disease to such personnel if it were to accidentally puncture them. Thus, health care personnel are in constant danger of contracting infections and diseases, some of which may be deadly. Other potential victims of accidental needle punctures include sanitation workers which later dispose of garbage containing the hypodermic needle. The diseases which may be transmitted by a contaminated hypodermic needle include Immune Deficiency Virus, Hepatitis, Rabies, Kure, Encephalitis, and Arbor viruses. The outcome of contracting one of these diseases is often fatal because there are no known cures for any of these diseases. Often a needle puncture in a person's skin is so trivial that it remains unrecognized until the person becomes seriously ill.

Existing OTN catheters suffer from penetration problems because of long length needles and unsecured needle supports. In addition, existing OTN catheters still present the danger of causing needle pricks due to ineffective encasement of the needles following use.

Accordingly, there exists a need for a hypodermic needle assembly which overcomes the above-noted drawbacks associated with existing assemblies.

The problem of suffering accidental needle punctures is well recognized. As a result, enormous inventive effort has been devoted to concealing the sharp needle point of hypodermic needles. One such effort is described in the present applicant's U.S. Pat. No. 5,338,311, issued Aug. 16, 1994.

SUMMARY OF THE INVENTION

A primary object of the present invention is to improve the syringe assembly described in the aforementioned U.S. Pat. No. 5,338,311.

One specific object of this invention is to provide an improved syringe assembly which provides good structural stability for the mechanism that is used to retract the needle after it has been used.

Yet another object of the present invention is to provide such an improved syringe assembly which facilitates fabrication, and reduces the cost, of the assembly.

Still another object of the present invention is to provide such an improved syringe assembly which facilitates the operation of the assembly, particularly when it is desired to retract the needle prior to disposing of the syringe assembly.

Another object of the present invention is to provide such an improved syringe assembly which improves the acceptability of the assembly by providing an external appearance which is virtually the same as that of conventional hypodermic needle assemblies which do not provide for needle retraction.

A further object of the invention is to provide such an improved syringe assembly that has the same length as conventional hypodermic needle assemblies which do not provide for needle retraction.

Other objects and advantages of the invention will become apparent upon reading the following detailed description and upon reference to the accompanying drawings.

In accordance with the present invention, the foregoing objectives are realized by providing a syringe assembly, operable in a normal mode and convertible to a retraction mode, comprising an elongated, generally cylindrical barrel forming a hollow nozzle located at the distal end of the barrel and opening into the interior of the barrel; a plunger slidably mounted in the barrel and forming a longitudinal cavity extending between the distal end and the proximal end of the plunger; a needle holder slidably mounted in the longitudinal cavity of the plunger; means forming a spiral channel extending along a proximal end portion of the barrel for retracting the needle holder within the barrel in response to relative rotational movement between the barrel and the plunger; and latching means on the barrel for latching and unlatching the needle holder at the distal end of a spiral channel.

In accordance with another aspect of the invention there is further provided an over-the-needle catheter and means for releasably securing the catheter to the above syringe assembly.

BRIEF DESCRIPTION OF THE DRAWINGS

FIG. 4 is an enlarged side elevation of a plunger of the assembly of FIG. 1;

FIG. 4a is a sectional view taken generally along the line 4a—4a of FIG. 4;

FIG. 5 is an end view of the plunger of FIG. 4;

FIG. 6 is a sectional view taken generally along the line 6—6 of FIG. 4;

FIGS. 7 and 8 are enlarged sections and FIG. 9 is an end view of two alternate forms of an end cap for the plunger of FIG. 4;

DETAILED DESCRIPTION OF THE ILLUSTRATED EMBODIMENTS

Figure 1:
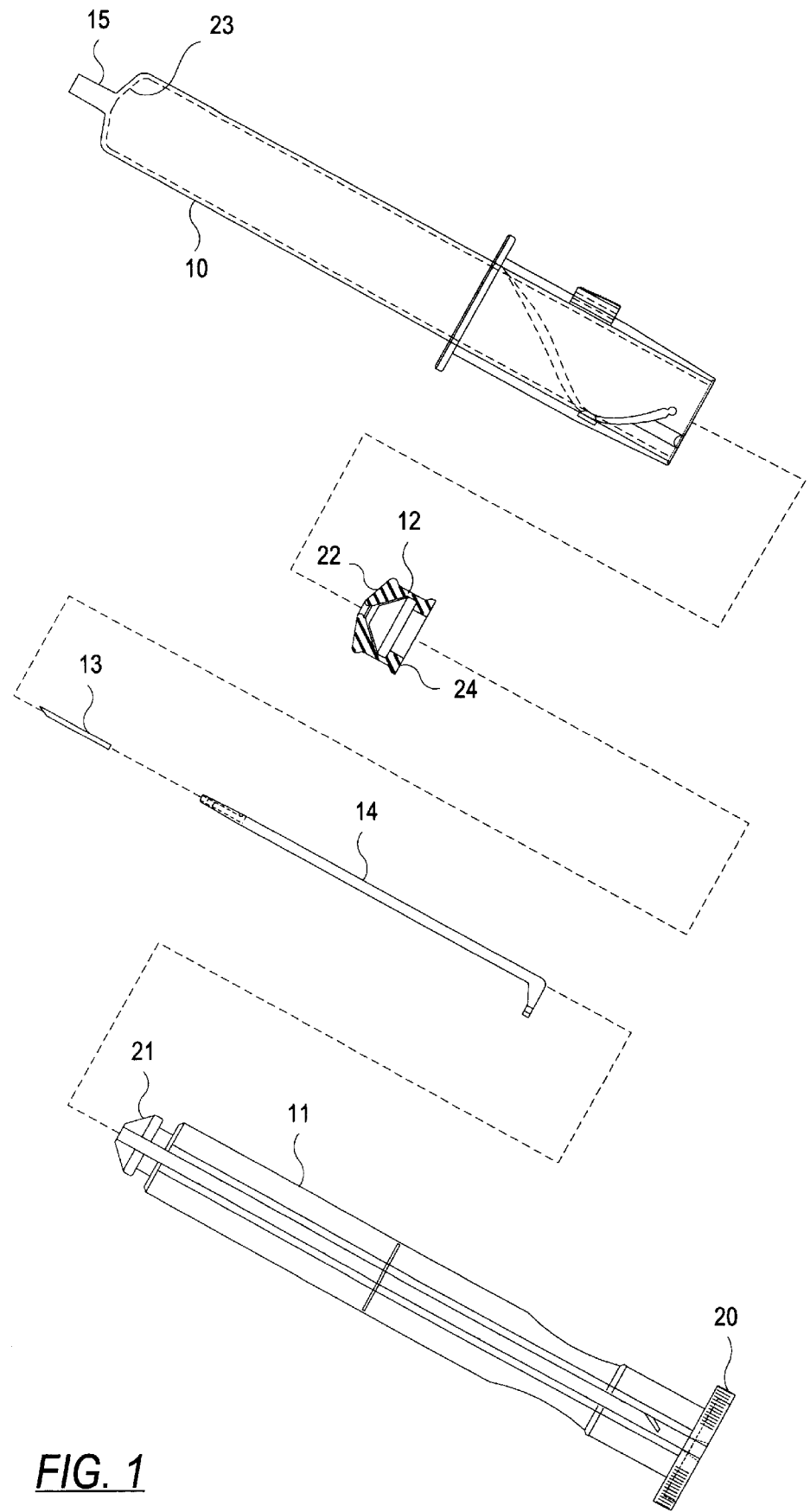
FIG. 1 is an exploded view of a syringe assembly embodying the present invention.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

Several different features of the invention are described, and permutations and combinations of these features will lead to further embodiments.

Turning now to the drawings, there is illustrated a syringe assembly including a barrel 10, a plunger 11, a hollow plunger cap 12, a hypodermic needle 13, and a needle holder 14. The barrel 10 is a hollow cylinder which terminates in a hollow tapered nozzle 15 at a distal end thereof. A tapered or conical wall portion 23 leads to the nozzle 15. Otherwise the barrel 10 has constant inner and outer diameters through a proximal end portion 16 thereof. The interior of the nozzle 15 communicates with the hollow interior of the barrel 10. An outwardly extending flange 17 nearer the proximal end of the barrel 10 facilitates gripping of the barrel with the user's fingers when it is desired to move the plunger 1 1 relative to the barrel 10. If desired, a portion of the outer surface of the barrel on the distal side of the flange 17 may be serrated to facilitate gripping of the barrel during relative rotation of the barrel and plunger, as decribed below. The proximal end of the barrel 10 is open.

The proximal end portion 16 of the barrel 10 has a spiral slot 19 through its wall. As will be described below, this spiral slot 19 provides a retraction track for the needle holder 14 and the hypodermic needle 13. The spiral slot 19 extends along a sufficient length to accommodate retraction of the needle holder 14 through a distance that is sufficient to draw the entire length of the needle 13 inside the barrel 10, as described in more detail below. To lessen the weakening of the wall of the distal end 16 of the barrel 10, the spiral slot 19 extends less than 360° about the circumference of the barrel 10. In the illustrative embodiment, the spiral slot 19 extends approximately 270° about the circumference of the barrel 10. The extent of the slot 19 could be less than 270° without departing from the invention.

The outer surface of the barrel 10 preferably contains graduations (not shown) indicating the volume level of fluid in the barrel. These graduations take into account the volume of the internal components such as the needle holder 14.

The proximal end of the plunger 11 forms a knob 20 that can be grasped by a user to effect linear or rotary movement of the plunger 11 relative to the barrel 10. The periphery of the knob 20 is serrated to facilitate gripping of the knob for rotary movement of the plunger. The distal end of the plunger 11 forms a head 21 to accommodate the hollow rubber plunger cap 12. The outside diameter of the resilient cap 12 is reduced in the central portion so that the cap engages the inside wall of the barrel 10 only at the pliable margins of the ends of the cap. The diameter of the engaging end portions of the cap 12 is slightly larger than the inside diameter of the barrel 10 so that the cap presses firmly against the inside wall of the barrel to form an air-tight and liquid-tight seal at the cap/barrel interface. The inner margins of the cap 12 make a similar tight contact with the outer surface of the needle holder 14. The inner margin of the cap 12 may be provided with a slit valve 12a (see FIGS. 6, 7 and 8) for this purpose, i.e., to seal against the outer surface of the needle 13 when it extends therethrough. The distal end 22 of the cap 12 is conical to conform to the conical distal end 23 of the inside surface of the barrel 10 when the plunger 11 is fully advanced within the barrel.

The head 21 of the plunger 11 is configured to fit tightly within the hollow plunger cap 12. With the cap 12 locked onto the head 21 of the plunger, the flat proximal end 24 of the cap abuts the flat surface of a circular disc 25 at the base of the plunger head 21. Due to the air-tight and liquid-tight seal between the plunger cap 12 and the barrel 10, as well as the needle holder 14, advancing movement of the plunger 11 inside the barrel 10 creates pressure in the interior of the barrel between the plunger cap and the distal end of the barrel. Similarly, retracting movement of the plunger 11 creates a partial vacuum in that portion of the barrel interior. Alternatively, a resilient barrel contacting with the rigid plunger plate 25 modified to carry a central elastic 0 ring can be used.

Figure 2:
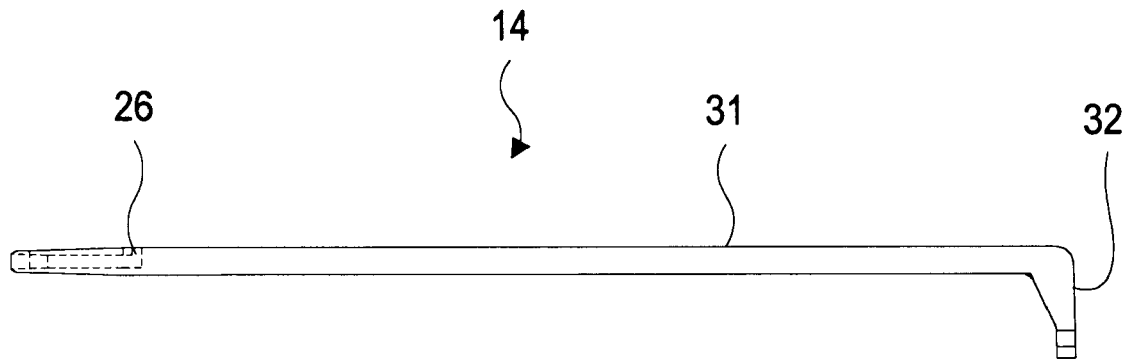
FIG. 2 is a side elevation, partially in section, of a needle holder included in the assembly of FIG. 1.
Figure 3:
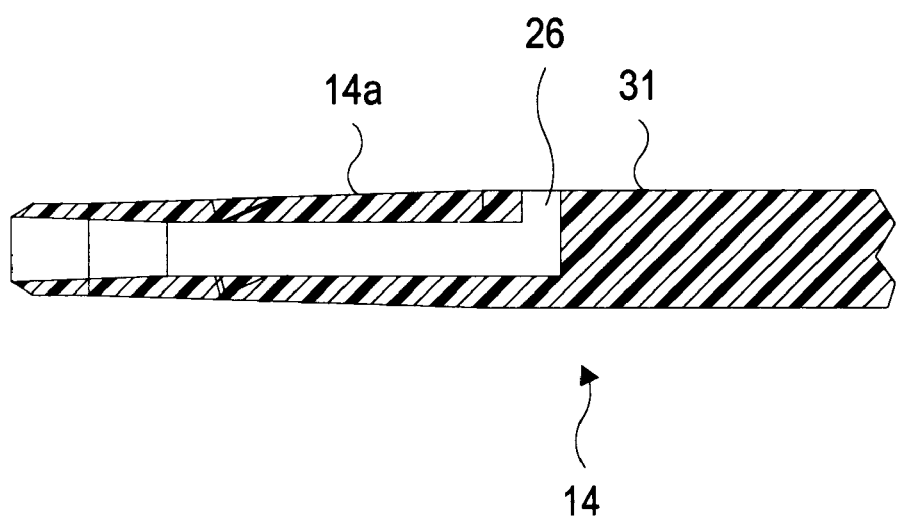
FIG. 3 is an enlarged partial elevation, partially in section, of a distal end part of the needle holder of FIG. 2.

The hypodermic needle 13 is mounted on the distal end of the elongated needle holder 14, which is detachably interlocked to the barrel 10. Prior to use of the syringe assembly, the needle 13 is covered by a protective cap (not shown) which prevents needle pricks and preserves sterility prior to use. Both the needle 13 and the distal portion of the needle holder 14 are hollow, and the interior of the hollow needle 13 communicates with the interior of the hollow distal portion of the needle holder 14. The needle holder 14 further communicates with the interior of the barrel 10 through an aperture 26 in the side wall of the hollow portion of the needle holder 14 (FIGS. 2 and 3). Prior to and during use of the syringe assembly for injection of medicine or withdrawal of blood (hereafter referred to as "normal use"), the aperture 26 is positioned at the base of the barrel nozzle 15. The aperture 26 permits blood or medicine to enter or exit from the barrel 10 via the needle holder 14 and the needle 13. This arrangement minimizes the dead space within which liquid can be retained in the syringe.

During normal use of the syringe assembly, the needle holder 14 is locked to the barrel 10, and the plunger 11 and its cap 12 are free to slide longitudinally back and forth along the needle holder. The needle holder 14 comprises an L-shaped rod having a longitudinal body portion 31 extending axially and including the aperture 26, and a lateral arm 32 extending radially across the barrel 10 at the proximal end of the rod.

To permit relative sliding movement between the plunger 11 and the needle holder 14 in the longitudinal direction, the needle holder is mounted in a longitudinal channel 33 formed as an integral part of the plunger 11. Multiple spaced apart resilient detents or retaining elements 34 (FIGS. 4 and 4a) project inwardly from the opposed walls of the channel 33 to hold the needle holder 14 within the channel. These detents or retaining elements 34 are deflected during insertion of the needle holder 14 into the channel 33, and then the elements 34 spring back to their original positions after the needle holder is in place. It will be noted that the ribs 60 and 62 that form the opposed walls of the channel 33 extend all the way to the inside wall of the barrel 10 (see FIG. 10), thereby constraining the lateral arm 32 of the needle holder against any angular or rotational displacement relative to the plunger 11. That is, the plunger 11 and the needle holder 14 can rotate only in unison with each other, although they are free to move independently of each other in the longitudinal direction. At the proximal end of the needle holder, a locking detent 75 (described below) locks the arm and plunger together to prevent relative longitudinal movement after retraction is complete.

To lock the needle holder 14 to the barrel 10, the outer surface of the distal end portion of needle holder 14 is seemlessly molded with a special texture to form a tapered surface 14a which mates with a complementary tapered surface 15a on the inside wall of the barrel nozzle 15. These tapered surfaces 14a and 15a are conventionally known as locking luer tapers, and the angle of the taper (typically expressed as a percentage of the diameter) is conventionally known as a locking taper angle. In a preferred embodiment, a 6% taper angle is used.

The locking surfaces 15a and 14a are engaged during assembly of the needle syringe, when the plunger 11 and needle holder 14 are inserted into the barrel 10 through the open proximal end of the barrel. The resultant locking luer taper can be released only by the application of simultaneous axial and rotational forces.

The proximal end of the needle holder 14 is also locked to the barrel 10, via the lateral arm 32. This arm 32 extends radially beyond the plunger and fits into the spiral slot 19. The arm 32 can be locked to the barrel 10 at the distal end of the spiral slot 19 and, when so locked, permits only reciprocal linear movement of the plunger 11, to create vacuum to withdraw medication or blood and pressure to deliver medication to the patient via the hypodermic needle. When the arm 32 is locked at either end of the slot 19, the plunger 11 cannot be rotated within the barrel 10. When the arm is locked in the detent 75 at the proximal end of the slot, it disables the entire syringe.

When the user desires to retract the hypodermic needle 13 within the barrel-plunger assembly, a mechanical latch 50 is manually actuated to unlock the arm 32 and thereby permit rotation of the plunger 11 relative to the barrel 10 along the spiral track 19. This relative rotation retracts and locks the needle-needle holder assembly within the barrel-plunger assembly. For the needle and needle holder to be moved to the retracted position, the plunger 11 can be in any desired position, e.g., to permit blood or medication to be retained in the syringe.

The preferred latch mechanism 50 of FIGS. 1 and 10–14 includes a longitudinally grooved tab 51 mounted for sliding movement upon a short longitudinal track 52 on the outer wall of the barrel 10. The groove 53 of the tab 51 is shaped to match the outer surface of the track 52 so that the tab 51 slides back and forth on the track 52. The outer surface 54 of the tab 51 is serrated to facilitate movement thereof with the user's finger or thumb.

The locking tab 51 also includes a small recess 56 formed within the groove 53. This recess 56 is sized and located to engage a terminal end part of the lateral arm 32 of the needle holder 14, when the lateral arm 32 is at a distal end portion of the spiral slot 19 with the needle 13 in a fully extended position. This prevents the tab from sliding in the proximal direction along the track 52. This engagement can be overcome by a deliberate manually applied force to retract the tab 51 when it is desired to retract the needle.

Figure 21:
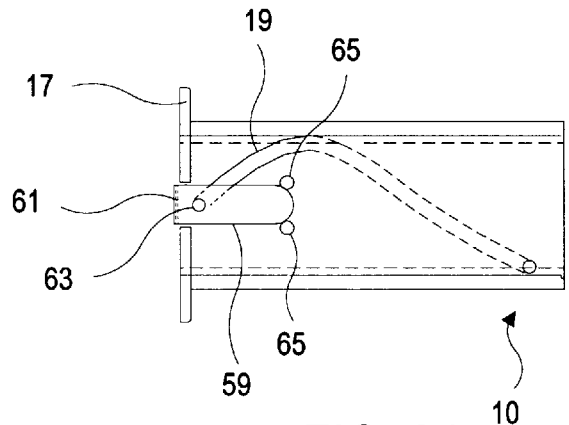
FIGS. 21 through 23 are elevations showing an alternate locking tab on the barrel.
Figure 22:
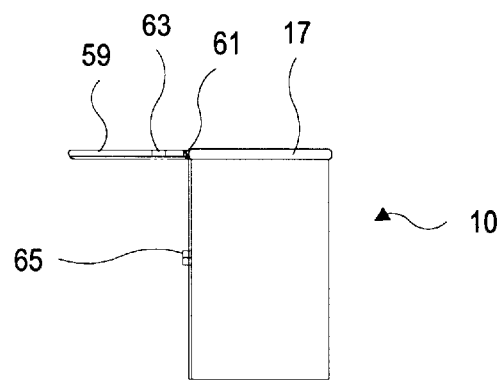
Figure 23:
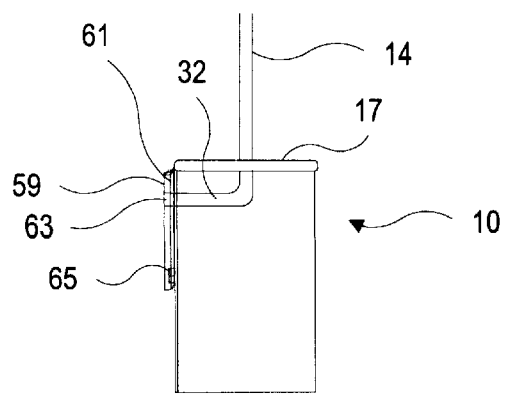

The latch 50 can be opened or closed by linear movement of the locking tab 51 along the track 52. During normal use, the needle holder arm 32 is positioned at the distal end of the spiral slot 19, which is immediately adjacent the flange 17, and the locking tab 51 is advanced on the track 52 to retain the arm 32 at the distal end of the slot 19. This locks the needle holder 14 in the normal operative mode in which only linear reciprocal movement of the plunger 11 is permitted. Because the locking tab 51 retains the arm 32, the needle holder 14 cannot rotate and thus cannot travel along the spiral slot 19 for retraction of the hypodermic needle 13. Alternatively, a hinged locking tab 59 (FIGS. 21–23) connected by a living hinge 61 to the barrel 10 may be provided. The tab 59 has a through aperture 63 for engaging the lateral arm 32 at the distal end of the slot 19. Detents 65 on the outer wall of the barrel 10 may hold the tab in place when engaged with the lateral arm 32 of the needle holder 14.

Figure 11:
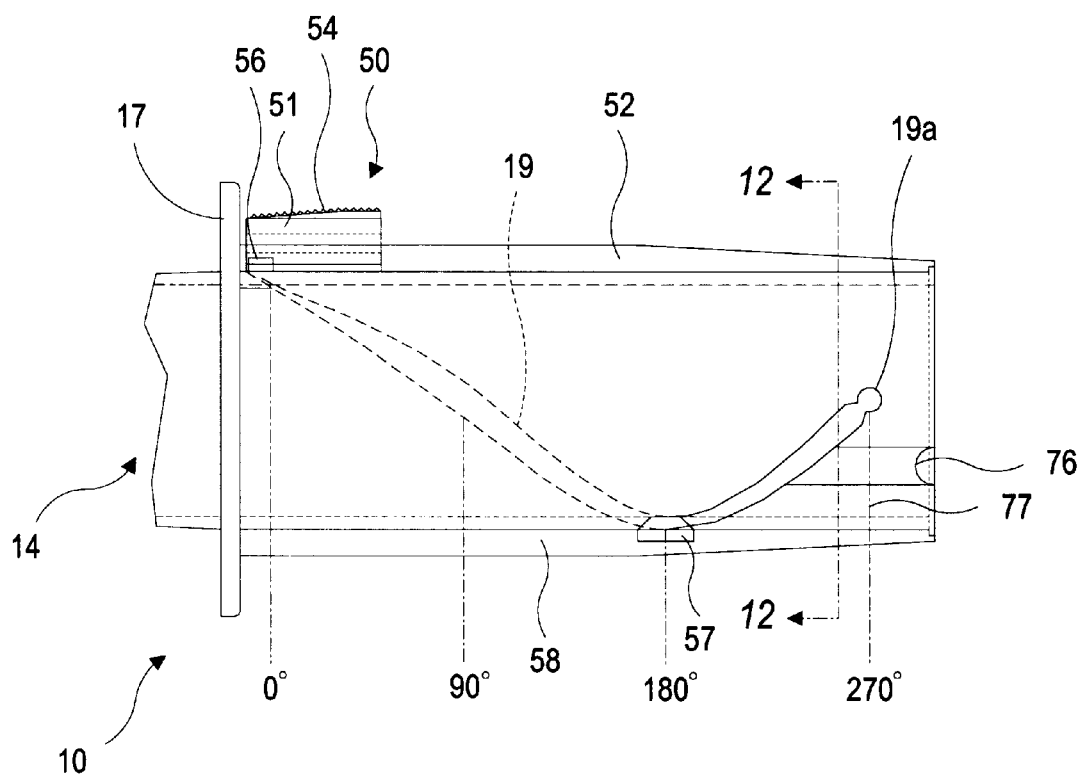
FIG. 11 is an enlarged partial side elevation of a barrel portion of the assembly of FIG. 9.
Figure 12:
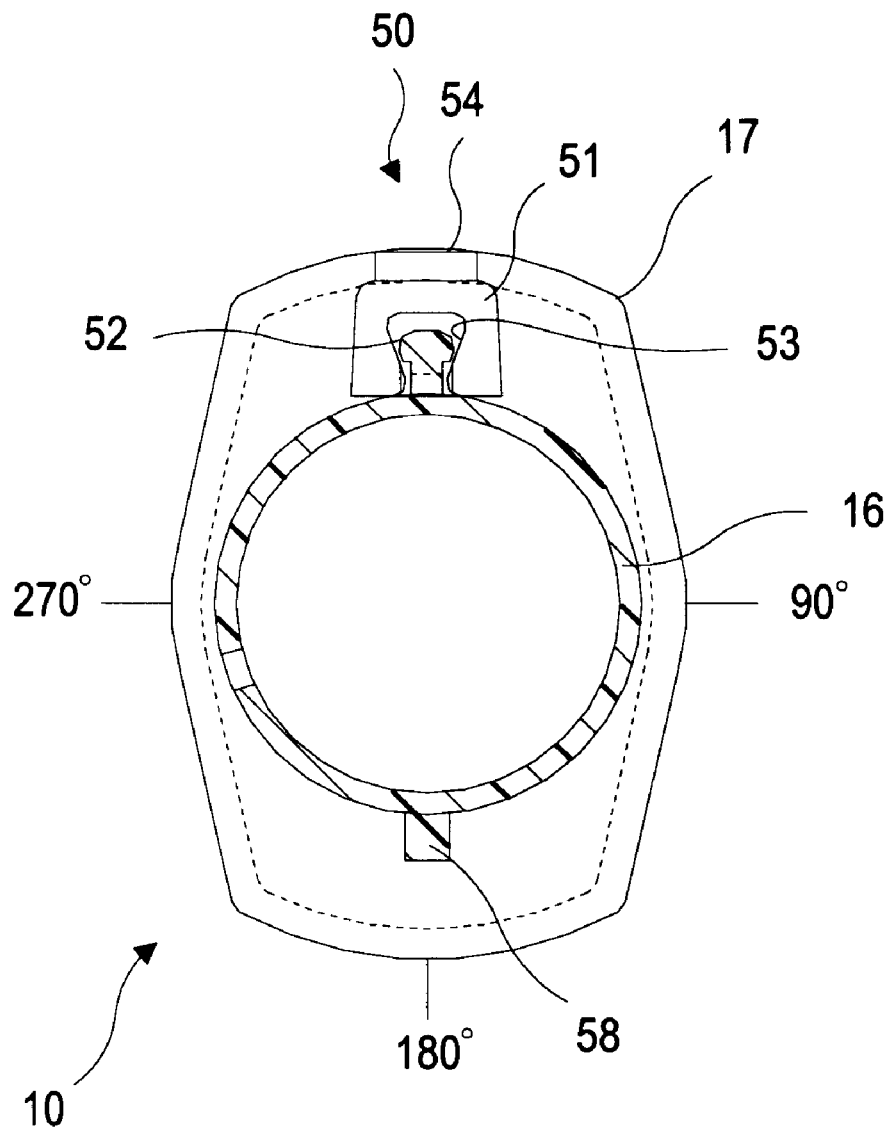
FIG. 12 is a view taken generally along the line 12—12 of FIG. 11.
Figure 13:
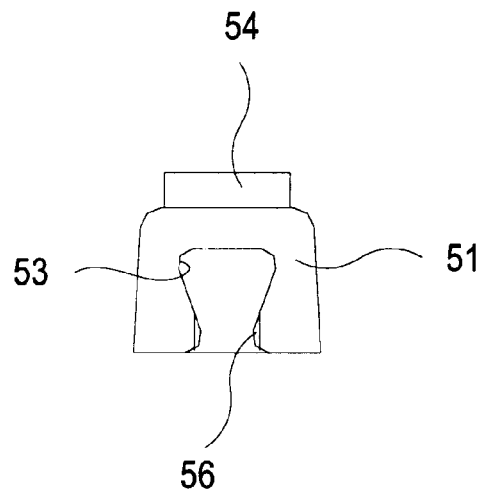
FIG. 13 is an enlarged end view of a locking tab of the assembly of FIG. 1.
Figure 14:
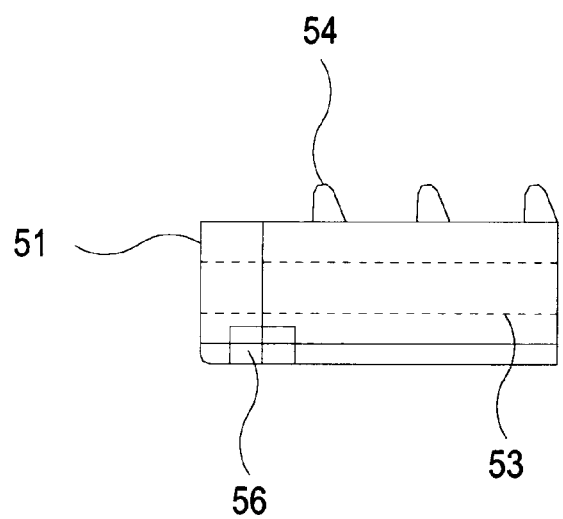
FIG. 14 is a side elevation of the locking tab of FIG. 13.

When it is desired to retract the needle, the tab 50 is retracted along the track 52 toward the proximal end of the syringe, thereby permitting rotation of the plunger 11 and retraction of the needle holder 14 by movement of the arm 32 along the spiral slot 19. Preferably, a proximal end of the spiral slot 19 includes a keyhole-shape locking feature 19a (FIG. 11) to lock the end of the arm 32 in place when the needle holder has been fully retracted. Also illustrated in FIG. 11 are the approximate positions of the lateral arm 32 of the needle holder 14 as it is rotated through 90°, 180° and 270° relative to the spiral slot 19. The needle holder 14 ascending proximally on the spiral 19 slot passes into the keyhole 19a and through the angular detent 75, snapping into the locked position with a click.

Figure 19:
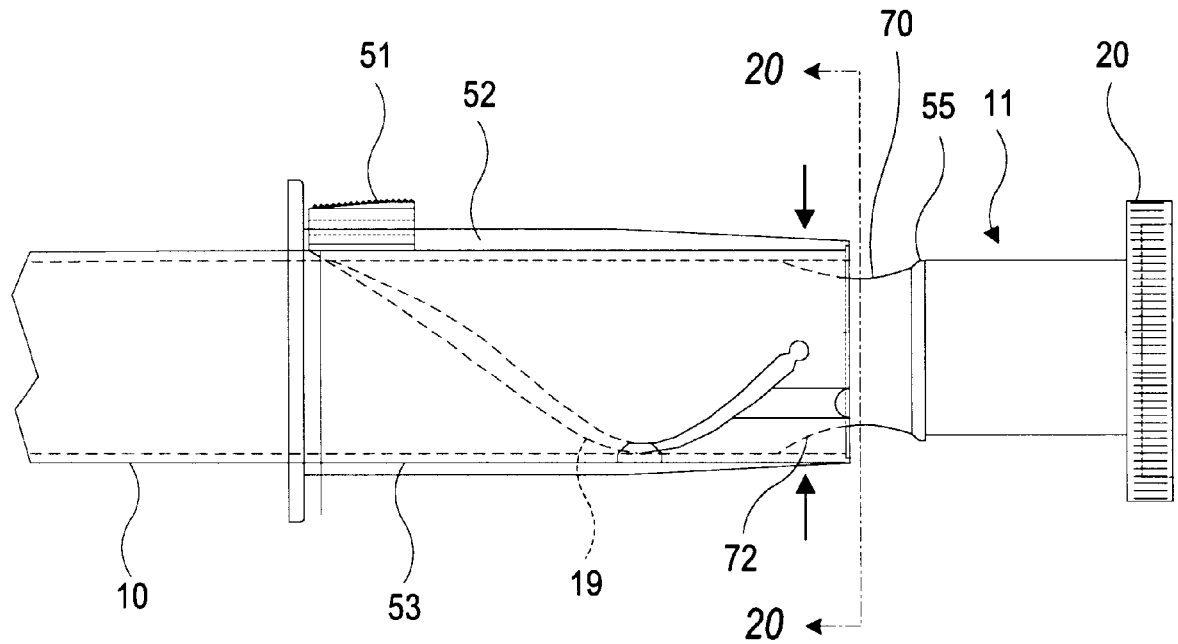
FIG. 19 is a partial side elevation of the syringe assembly, illustrating a part of the procedure for assembly of the plunger and needle holder with the barrel.
Figure 20:
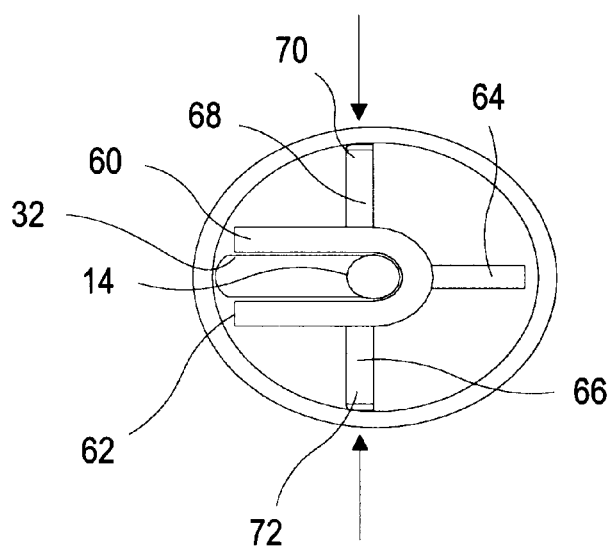
FIG. 20 is a partial sectional view taken generally along the line 20—20 of FIG. 19.

Referring again to FIGS. 4 and 9, and also to FIGS. 19 and 20, the plunger 11 will be seen to have a plurality of ribs which extend radially outwardly at substantially 90° intervals. A first pair of these ribs 60, 62 define the longitudinal channel 33 for holding the needle holder 14 as described above. A single rib 64 projects diametrically oppositely of these ribs 60 and 62. A further pair of diametrically oppositely extending ribs 66 and 68 are formed in a plane at right angles to the ribs 60, 62 and 64. In accordance with a preferred form of the invention, these latter ribs 66 and 68 include recessed surfaces 70, 72 toward their proximal ends.

Figure 10:
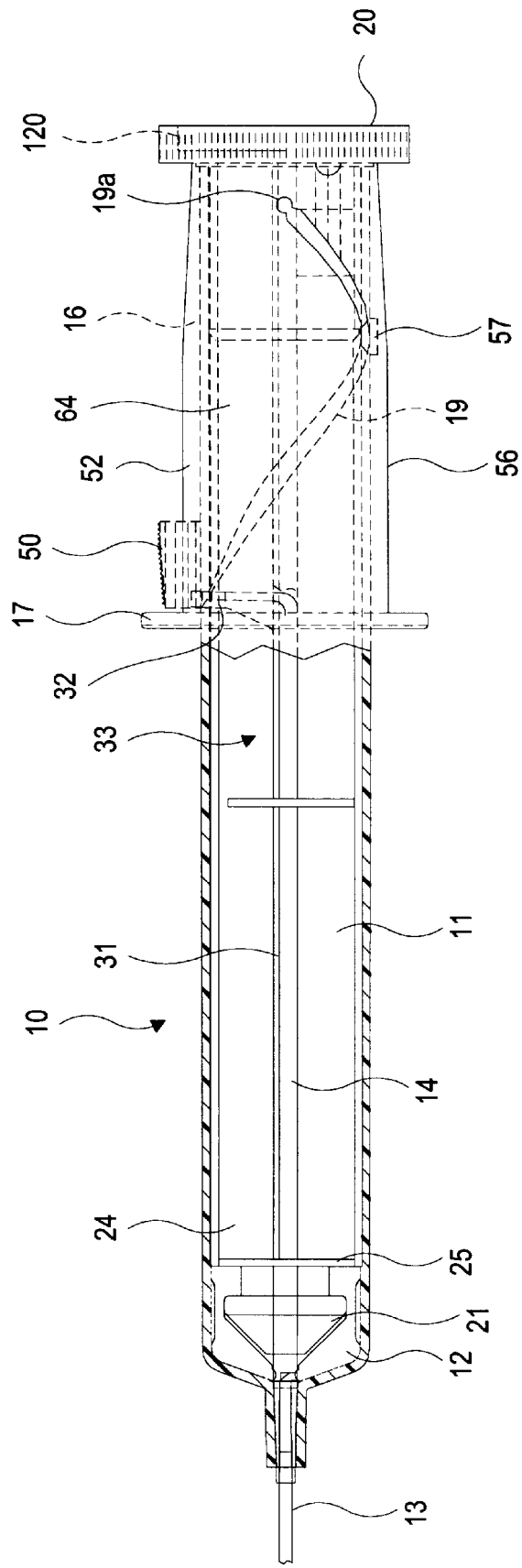
FIG. 10 is an enlarged side elevation of the syringe assembly of FIG. 1 with the needle holder in the advanced position and the plunger in its fully advanced position.

As shown in FIG. 10, a transverse rectangular slot 110 in the plunger 11 forms an access slot for a mold insert to form the detent 75, and a hole 120 (FIG. 5) in the plunger head 20 provides access for a tool used to push the needle holder 14 longitudinally into the barrel 10 during initial assembly of the syringe (after the needle holder has been snappingly engaged beneath the detents 34 of the channel 33).

Referring to FIGS. 19 and 20, with the plunger 11 partially withdrawn with respect to the barrel 10, the recessed surfaces 70 and 72 of the ribs 66 and 68 provide a relief space for a proximal end part of the barrel 10 when the open end of the barrel 10 is pressed together, for example by applying pressure between a thumb and a finger. As best viewed in FIG. 20, this action momentarily distorts the proximal open end of the barrel 10 to a somewhat elliptical shape so as to permit the initial insertion of the lateral arm portion 32 of the needle holder 14 past the proximal open end of the barrel 10 and into the spiral slot 19. An indexing recess 76 (FIG. 11) in the end of the barrel 10 holds the needle holder 14 in the correct angular position during assembly, and a shallow channel 77 (FIG. 11) further facilitates insertion of the needle holder 14 into the barrel 10 while the barrel is temporarily distorted to its elliptical shape. When the pressure on the barrel 10 is released, it resumes its generally circular cross-sectional shape for retaining the lateral arm 32 in engagement with the spiral slot 19.

It will be appreciated that when the tab 51 is retracted to unlock the arm 32, the plunger can be in any desired longitudinal position. That is, the plunger can be fully advanced, fully retracted, or at any intermediate position. This is advantageous because it might be desired to retract the needle after only a portion of a dose of medication has been injected into the patient, or it might be desired to retain a portion of a blood sample withdrawn from a patient within the syringe. To prevent the leakage of any fluid contained within the syringe at the time the needle is retracted, a latex seal (not shown) may be provided at the end of the nozzle 15, or a needle cap 78 (FIG. 18) may be utilized.

To ensure retention of the end portion of the arm 32 within the spiral slot 19 during retracting movement of the needle holder 14, the plunger 11 includes an integral circular retaining plate 55. The diameter of this plate 55 matches the inside diameter of the guide barrel 10 so that it tends to maintain the desired circular shape of the inside wall of the barrel 10. Stresses exerted on the wall of the barrel during use can tend to distort its desired circular configuration, and if the distortion becomes large enough, the arm 32 can escape from the spiral slot 19. With the retainer plate 55 riding on the inside wall of the barrel 10, however, such excessive distortion is prevented, and thus retention of the arm 32 within the spiral slot 19 is ensured. Of course, in addition to the retainer plate 55, the longitudinal ribs of the plunger also glide on the inside wall of the barrel 10 at approximately 90° intervals from each other, and thus further ensure that the barrel retains its desired circular configuration.

A number of other features of the design of the barrel 10 help to retain the shape of the barrel 10, particularly in the region of the spiral slot 19, so as to further assist in retaining the arm 32 within the spiral slot 19. One of these features is the design of the spiral slot 19 itself, which, as mentioned above, extends less than 360° around the circumference of the barrel. In the illustrative embodiment, the spiral slot extends only around approximately 270° of the circumference of the barrel 10. The extent of the slot could be even less than 270° without departing from the invention. Also, the track 52 and a diametrically opposed similarly raised rib 58 are integrally formed in the side wall of the proximal end portion of the barrel 10 preferably running longitudinally from its proximal end to the flange 17. These raised ribs 52, 58 further assure the structural integrity and rigidity of this portion of the barrel 10. Additional reinforcement may be provided by increasing the thickness of the barrel wall in this proximal region, or by the use of a different material in the segment of the barrel containing the spiral slot. A through slot 57 is provided at a suitable point in the rib 58 to permit the end part of the arm 32 to pass thereby as it slides along this portion of the spiral slot 19.

During normal use of the syringe assembly, the barrel 10 and the needle holder 14 are held stationary, and the plunger 11 is free to move longitudinally relative to both the barrel 10 and the needle holder 14. Advancing movement of the plunger 11 is limited by contact of the plunger cap 12 with the end wall of the barrel 10, as shown in FIG. 9. Retracting movement of the plunger 11 is limited by contact of the plunger disc 25 with the arm 32. If desired, an internal ring 79 (FIG. 11) may be provided on the inside surface of the barrel to engage the disc 25 on the distal side of the spiral slot 19, to prevent further retraction of the plunger and protect against the leakage of fluids through the spiral slot 19 in the barrel wall.

The needle holder 14 is locked to the barrel 10 by virtue of the taper lock between the distal portion of the needle holder and the barrel nozzle 15, and the forced or strained locking engagement of the lateral arm 32 by the tab 51. Alternatively, the needle holder can be locked to the nozzle by a threaded connection, as described in more detail in my prior U.S. Pat. No. 5,643,222. The plunger 11 is also free to move longitudinally relative to the needle holder 14 because the needle holder is not locked to the plunger in that direction. The locking of the lateral arm 32 by the tab 51 prevents rotational movement of the plunger as well as the needle holder, and also prevents the plunger from being accidentally pulled out. As long as the lateral arm 32 of the needle holder is locked by the tab 51, the syringe assembly is in its normal operating mode.

Following normal use of the syringe assembly, the needle 13 can be retracted into the plunger 11 and the barrel 10. This requires axial movement of the needle holder 14 within the barrel 10 toward the proximal end thereof, which in turn requires that the needle holder 14 be unlocked for movement along the spiral slot 19. Thus, to initiate retraction of the needle holder 14, the arm 32 is unlocked by retracting the tab 51.

Figures 15, 16, 17, 18:
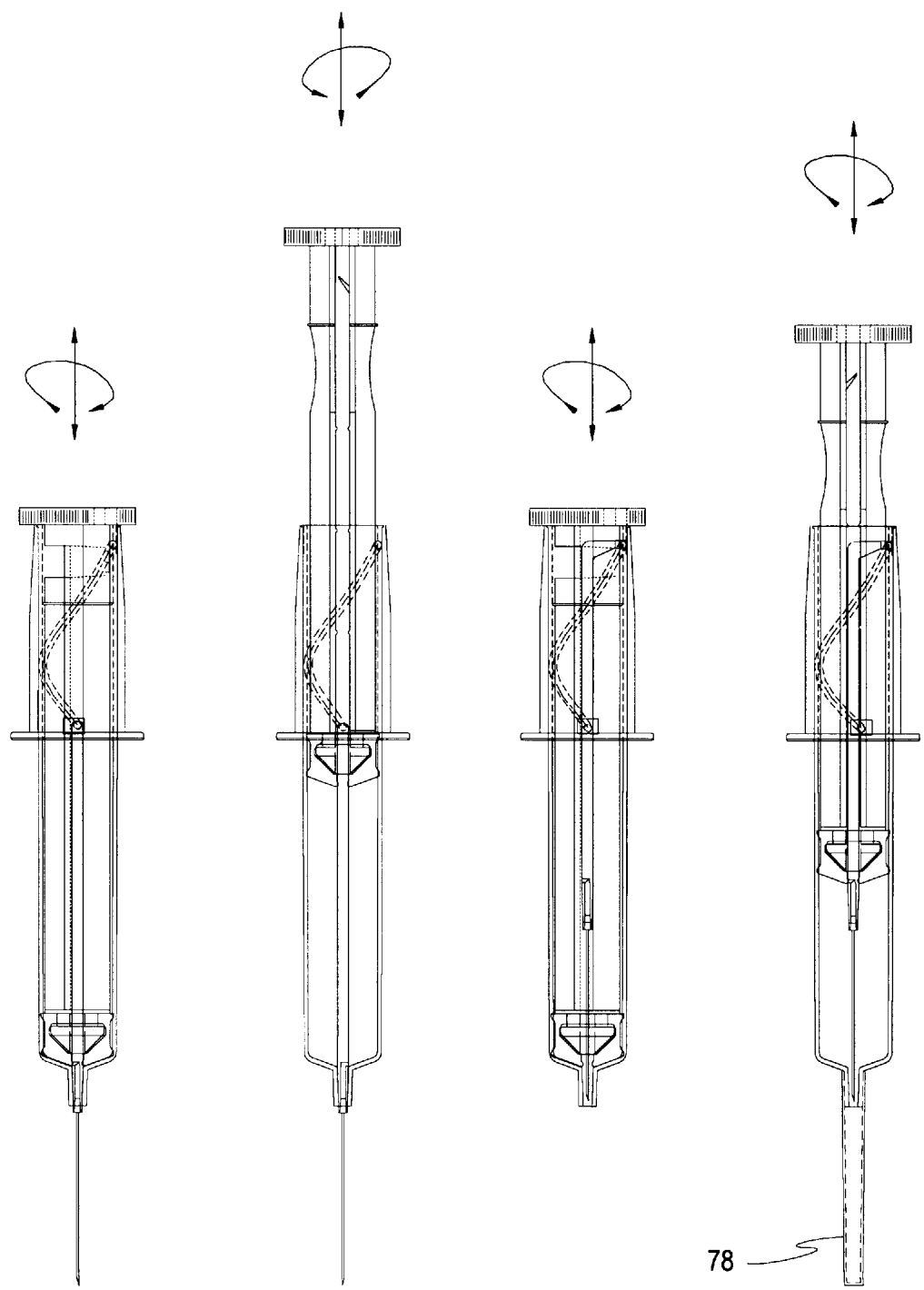
FIGS. 15 and 16 are diagrammatic illustrations of the syringe assembly of the invention showing the available range of axial movement of the plunger and with the needle fully advanced.
FIGS. 17 and 18 are diagrammatic illustrations of the syringe assembly showing the available range of axial movement of the plunger relative to the barrel and with the needle holder in the retracted position and the needle concealed by the barrel.

After the tab 51 has been retracted, the plunger knob 20 is turned to rotate the plunger 11 clockwise (as viewed from the proximal end) relative to the barrel. As the plunger is rotated, the needle holder 14 rotates in unison with the plunger because the arm 32 is captured between the opposed parallel walls of the channel 33 in which the needle holder is mounted in the plunger. Rotation of the needle holder 14 relative to the barrel (1) retracts the needle holder within the plunger by the camming action of the wall of the spiral slot 19 acting on the arm 32, and (2) releases the locking luer taper at the distal end of the barrel nozzle 15 due to the resulting compound rotational and longitudinal forces applied to the tapered surfaces 15a and 14a. As rotation continues, the arm 32 traverses the entire length of the spiral slot 19, thereby retracting the entire needle holder 14 through a corresponding axial distance within the plunger 11 (see FIG. 17). Of course, the needle 13 is retracted along with the needle holder 14, and thus the needle is retracted completely within the barrel nozzle 10 and the plunger 11, as illustrated in FIG. 17.

In the illustrative embodiment, the spiral slot 19 is formed in a proximal end portion of the barrel 10. The spiral slot preferably has a constant rate of curvature along its length and as noted above preferably extends only (approximately) 270° or less about the circumference of the barrel 10. The illustrative syringe need not be any longer than a conventional syringe because conventional syringes are made longer than required to provide more than the desired fluid volume, so as to avoid inadvertent withdrawal of the plunger and the resultant spillage of the syringe contents. The extra barrel length also accommodates the spiral slot 19 in the space between the plunger knob and the finger flanges. Thus, the present invention permits the extension of the barrel length in this area to be used for the needle-retracting mechanism.

At the distal end of the spiral slot 19, the end of the arm 32 physically bends the detent 75 and snaps into the keyhole-shaped detent notch 19a (FIGS. 1, 10 and 11) formed by the walls of the slot so that the user feels a click at the end of the needle retraction. The locking action is automatic. Then if the user attempts to turn the plunger knob 20 in the opposite direction, such attempt is met with firm resistance. This is a safety feature to prevent the needle from being returned beyond the end of the barrel nozzle, and to discourage re-use of the syringe.

A proximally inwardly divergent locking detent 75 (FIG. 4) is formed projecting from the inside wall of the channel 33 near the proximal end thereof to prevent the plunger 11 from being withdrawn from the barrel 10 after the needle holder 14 has been retracted. The arm 32 deflects the detent 75 as the arm is retracted past the detent, but the arm 32 then engages the proximal end of the detent so as to block any effort to retract the plunger 11 over the needle holder 14. This locking of the arm 32 by detent 75 also prevents further rotation of the plunger. The plunger knob 20 also blocks movement of the arm 32, and hence of the needle holder 13 and needle 14, back in the proximal direction.

To operate the syringe assembly, the protective cap 78 (FIG. 18) is removed from the needle 13, and the required amount of medication is aspirated into the barrel 10. Next, the injection site on the body of a patient is determined and the skin is cleaned with an antiseptic solution. Following percutaneous entry of the needle into the patient, location of the needle tip in the vein is confirmed by aspirating a small amount of blood into the transparent barrel 10. The plunger 11 is then advanced to force the medication from the barrel 10 into the vein. After the medication is administered, the needle 13 is withdrawn from the patient, the tab 51 is retracted to release the arm 32, and the plunger knob 20 is rotated clockwise until the user feels the arm 32 snap into the detent notch 19a at the proximal end of the spiral slot 19. The spiral slot 19 may alternatively be configured to require counterclockwise, instead of clockwise, rotation of the plunger knob 20. With the needle 13 completely retracted inside the barrel 10, the syringe assembly can be safely discarded in its entirety.

It can be seen from the foregoing description that the syringe assembly performs all the conventional functions of injection syringes and yet, upon completion of injection, the hypodermic needle 13 is concealed within the barrel 10. The syringe assembly can receive and disperse medications any number of times for a given patient by reciprocal longitudinal movement of the plunger 11 within the barrel 10. Another advantage of the syringe assembly is that its design prevents the plunger 11 from slipping out of the barrel 10 during normal use of the assembly.

The syringe assembly of this invention is easy to manufacture, cost-effective, and easy to use in the field. The parts can all be made by conventional plastic molding and using readily available metal needle stock. The plastic parts can be made by injection molding medical grade polymers such as polypropylene. The plunger seal or cap can be molded from natural or synthetic elastomeric polymers. The spiral channel within the wall of the barrel is molded by slides having spiral elevations contacting the core pin. The mold is not opened until the barrel is stripped off the core pin to preserve the integrity of the molded spiral track. The detents within the plunger channel 33 are molded by pins projecting inside the core of the plunger channel.

The final assembly is compact because the needle holder 14 is retracted directly into the plunger 11 itself, and thus the plunger 11 need not be fully withdrawn for needle retraction to occur. When discarded following use, the syringe assembly contributes minimally to the bulk of refuse. Since retraction of the needle 13 is effected, by turning the plunger knob 20 at the proximal end of the assembly, the hand of a user does not come into the vicinity of the needle point, thereby minimizing the possibility of a needle prick during retraction. Moreover, the assembly employs substantially the same number of components as conventional syringes, and does not require additional guards, sheaths, sleeves, springs, etc. to conceal the needle following use.

Figure 24:
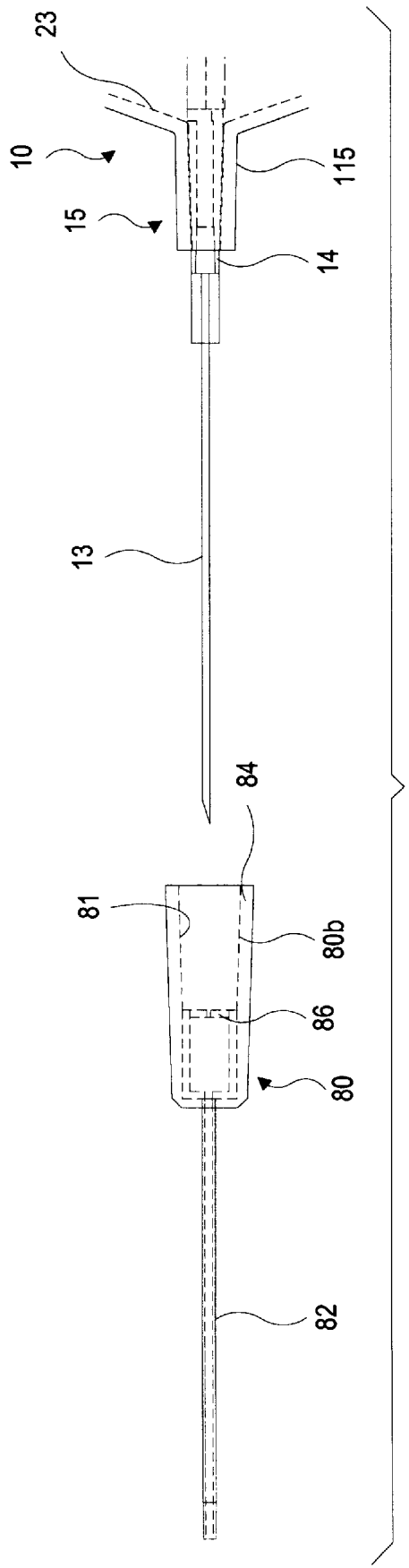
FIG. 24 is an enlarged cross-section of an over-the-needle catheter and a portion of the syringe assembly of FIGS. 1–20 embodying the present invention.

FIG. 24 depicts an over-the-needle ("OTN") catheter assembly including an OTN catheter 80 and the syringe assembly of FIGS. 1–20 (only a distal end portion of which is illustrated) with a hypodermic needle 13 mounted therein. In the embodiment of FIG. 24, the OTN catheter 80 is a polymeric catheter having an elongated tip 82 mounted thereto. Prior to use of the OTN catheter assembly, a proximal end surface 84 of the OTN catheter 80 is coaxially mounted over the nozzle 15 and the hypodermic needle 13 protrudes through both the nozzle 15 and the OTN catheter 80. The elongated tip 82 of the catheter 80 is advanced over the needle 13. Prior to use, i.e., prior to inserting the needle 13 and catheter tip 82 into a vein, the needle 13 and catheter tip 80 are enclosed by a removable cap (not shown).

Preferably, the catheter 80 includes an internal valve, such as a slit valve 86 to restrict the flow of fluids therethrough. Prior to and during normal use of the OTN catheter assembly, the OTN catheter 80 is held engaged over the nozzle 15 of the syringe assembly by locking luer tapers on the outer surface 115 of the nozzle 15 and the inner surface 81 of the catheter 80. Following puncture of the vein of a patient and insertion of the tip 82 of the OTN catheter 80 into the vein, the needle carrier 14 and the mounted needle 13 are retracted in the manner described above. At this retracted position the needle carrier 14 is irretrievably locked in place inside the barrel as described above. The syringe is then disengaged from the catheter by simultaneously rotating and withdrawing the syringe, so as to release the locking luer taper formed by surfaces 115 and 81, as shown in FIG. 24. The OTN catheter 80 is then advanced into the vein, and secured to the skin by adhesive tapes.

The purpose of the locking luer taper formed by surfaces 115 and 81 is to mechanically unify the syringe with the OTN catheter so that insertion force applied to the syringe is directly transmitted to the hypodermic needle 13 and catheter 80. Release of the locking luer taper disassociates this mechanical unity, permitting the syringe (with the needle 13 retracted) to be moved from the catheter 80.

During puncture of the vein, confirmation that the needle 13 and catheter tip 82 are located in the vein can be made by viewing blood entering the catheter 80 by capillary action. It, however, is also possible to confirm a flashback within the syringe barrel by partially retracting the plunger 11 relative to the barrel 10 to assure that continuity between the needle 13 and the vein is established. The side aperture 26 of the needle holder 14 opens up into the flashback chamber thus created. Confirmation of proper insertion in the vein is indicated by blood entering the barrel chamber via the side aperture 26 in the needle holder 14.

To use the OTN catheter-syringe assembly, the skin of a patient is first prepared and a peripheral vein is made prominent. Under aseptic precautions the vein is punctured with the needle 13 and catheter tip 82, and the location of the needle tip is judged by the change in color under the catheter or by the appearance of blood in the catheter or the flashback chamber. Once the location of the needle tip is confirmed, the needle carrier is retracted in the manner described above. While advancing and retaining the OTN catheter 80 in the vein, the syringe assembly is removed and an intravenous line is connected to the catheter 80. Finally, the catheter 80 is secured to the skin of the patient by adhesive tape.

Figure 25:
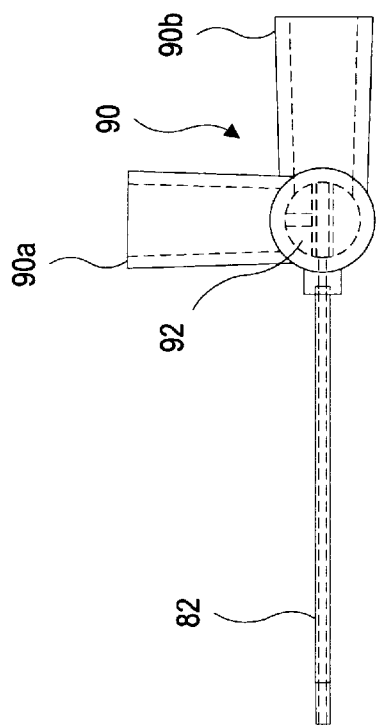
FIG. 25 is a cross-section similar to FIG. 24 showing another embodiment of an over-the-needle catheter.

As shown in FIG. 25, it is possible to replace the OTN catheter 80 with the slit valve 86 with an OTN catheter assembly 90 having two orthogonally disposed body portions 90a and 90b, which are operatively coupled to the elongated catheter tip 82 by a rotary-type 3-way ball valve mechanism 92. The elongated catheter tip 82 is the same as that of the catheter 80 of FIGS. 24–26.

The novel and improved syringe assembly as described above offers a number of advantageous features:

The detents 34 in the plunger channel 33 add precision to the needle holder movement. For example, straight axial retraction of the needle in the plunger channel 33 avoids angulation of the needle and puncture of the barrel cavity. It does not require extending the overall length of the syringe, and avoids the need for special measures such as breaking the plunger to prevent re-use.

The spiral track 19 is molded in the barrel itself and offers positive engagement of the needle holder without requiring additional arts or complexity.

The proximal end part 16 of the barrel 10 is strengthened by reducing the circumference of the spiral slot 19 from 360° to 270° or even further. Additional linear reinforcing ribs 52, 50 of material are incorporated in the barrel for strength.

The number of the components (except for the locking tab 51) in the present invention is the same as in a conventional syringe to keep it cost effective.

Use of the sliding needle holder eliminates the usual needle holder on the barrel nozzle, which eliminates the associated dead-space and quantity of wasted medications left over in the syringe nozzle and the female needle holder.

The operation of syringe is one-way so that accidental misuse is minimized, i.e., once retracted the needle holder is locked in place, so the needle cannot be re-extended.

Operation of the syringe is particularly safe because all the required manipulations of the various parts of the syringe are performed at or near the proximal end of the syringe, well away of the needle, during both the normal and retracting modes of operation.

The locking and disablement is automatic when the needle holder is retracted by rotating the plunger and is positively indicated by an audible click produced by the detent 75. Pull-back of the plunger is also blocked by the detent 75 in the plunger while the back-tracking of the needle holder in the spiral slot is also blocked by both the detent 75 and the interfering contact of the plunger knob and barrel margin and keyhole detent 19a.

In the rare event when only a partial dose of medicine is given to the patient, the syringe with leftover medicine can be rendered safe by rotary retraction of the needle holder, while capping of nozzle will prevent spillage.

It should be noted that the syringe assembly as described may be used to dispense medication or as a blood collection device. It may also be used to place an over-the-needle catheter, as described above.

While the present invention has been described with reference to one or more particular embodiments, those skilled in the art will recognize that many changes may be made thereto without departing from the spirit and scope of the present invention. Each of these embodiments and obvious variations thereof is contemplated as falling with the spirit and scope of the claimed invention, which is set forth in the following claims.

What is claimed is:

1. A syringe assembly, comprising:
    an elongated, generally cylindrical barrel having a hollow interior forming a hollow nozzle located at a distal end of said barrel and opening into the interior of said barrel;
    a plunger slidably mounted in said barrel and forming a longitudinal cavity;
    a needle holder slidably mounted in said longitudinal cavity of said plunger and having a lateral arm;
    means defining a spiral channel on said barrel extending along a proximal end portion of said barrel for engaging said lateral arm of said needle holder and retracting said needle holder within the barrel in response to relative rotational movement between the barrel and the needle holder;
    said barrel including means for strengthening said proximal end portion of said barrel; and
    latching means on said barrel for latching and unlatching said needle holder at a distal end of said spiral channel.

2. The syringe assembly of claim 1 wherein said latching means comprises a locking element slidably mounted on said barrel for reciprocating movement between a locking position at said distal end of said spiral channel and a non-locking position away from said distal end of said spiral channel.

3. The syringe assembly of claim 2 wherein said latching means includes means defining a groove on said locking element and a longitudinal track on an outer surface of said barrel for engaging said groove for effecting sliding movement of said blocking element.

4. The syringe assembly of claim 1 wherein said barrel includes an outwardly extending finger flange to facilitate gripping of the barrel, and the distal end of said spiral channel terminates at said flange.

5. The syringe assembly of claim 4 wherein said lateral arm extends radially into the spiral channel and wherein said latching means is moveable to capture the lateral arm of said needle holder in said spiral channel at a point adjacent to said flange.

6. The syringe assembly of claim 1 wherein said needle holder lateral arm extends laterally through said plunger cavity to said spiral channel, and said latching means is mounted for movement into and out of registry with a distal end of said spiral channel for capturing and releasing said lateral arm at the distal end of said spiral channel.

7. The syringe assembly of claim 1 which includes a hollow needle attached to the distal end of said needle holder.

8. The syringe assembly of claim 1 wherein said spiral channel is formed in the wall of said barrel and extends radially through the wall of said barrel.

9. The syringe assembly of claim 1 wherein said spiral channel includes means at a proximal end thereof for resisting advancing movement of said needle holder after it has been fully retracted.

10. The syringe assembly of claim 1 wherein said longitudinal cavity of said plunger includes a plurality of detent means for slidably retaining said needle holder within said longitudinal cavity.

11. The syringe assembly of claim 1 wherein said spiral channel extends less than 360° about the circumference of said barrel.

12. The syringe assembly of claim 1 wherein said means for strengthening comprises at least one longitudinal rib formed along the proximal end portion of said barrel and extending approximately the length of said spiral channel.

13. The syringe assembly of claim 12 wherein two of said longitudinal ribs are located substantially 180° apart on the outer circumference of said barrel.

14. The syringe assembly of claim 1 wherein said means for strengthening comprises a pair of diametrically opposed longitudinal ribs formed along the proximal end portion of said barrel.

15. The syringe assembly of claim 12 wherein said latching means includes a locking element and wherein one of said ribs defines a track on which said locking element is slidably mounted for movement between a locking position at a distal end of a spiral channel and a non-locking position away from said distal end of said spiral channel.

16. The syringe assembly of claim 1 wherein the needle holder lateral arm is engaged in said longitudinal cavity of plunger for causing said needle holder to rotate in unison with said plunger.

17. The syringe assembly of claim 16 wherein said plunger is rotatable relative to said barrel for causing said lateral arm to move along said spiral channel.

18. The syringe assembly of claim 1 wherein said needle holder includes a lateral arm for engaging the spiral channel and said barrel has an open end and said plunger includes recesses alignable with said open end of said barrel for defining a relief space for deformation of said open end of barrel to permit initial insertion of said lateral arm of said needle holder past said open end of said barrel and into said spiral slot.

19. A syringe assembly, comprising:
an elongated, generally cylindrical barrel forming a hollow nozzle located at the distal end of said barrel and opening into the interior of said barrel;
a plunger slidably mounted in said barrel and forming a longitudinal cavity;
a needle holder slidably mounted in said longitudinal cavity of said plunger and having a lateral arm;
said barrel forming a spiral channel extending along a proximal end portion of said barrel for engaging said lateral arm of said needle holder and retracting said needle holder within the barrel in response to relative rotational movement between the barrel and the needle holder, said spiral channel extending through the wall of said barrel, and
said barrel including reinforcing means to counteract the weakness caused by said spiral channel in said proximal end portion of said barrel.

20. The syringe assembly of claim 1 wherein said spiral channel extends less than 360° about the circumference of said barrel.

21. A syringe assembly, comprising:
an elongated, generally cylindrical barrel having a hollow interior forming a hollow nozzle located at a distal end of said barrel and opening into the interior of said barrel;
a plunger slidably mounted in said barrel and forming a longitudinal cavity;
a needle holder slidably mounted in said longitudinal cavity of said plunger and having a lateral arm;

means defining a spiral channel extending along a proximal end portion of said barrel for engaging said lateral arm of said needle holder and retracting said needle holder within the barrel in response to relative rotational movement between the barrel and the needle holder;
latching means on said barrel for latching and unlatching said needle holder at a distal end of said spiral channel; and
a pair of strengthening ribs extending along at least a part of said proximal end portion of said barrel.

22. The syringe assembly of claim 21 wherein said latching means includes a locking element and wherein one of said strengthening ribs defines a track on which said locking element is slidably mounted for movement between a locking position at a distal end of a spiral channel and a non-locking position away from said distal end of said spiral channel.

23. A syringe assembly, comprising:
an elongated, generally cylindrical barrel having a hollow interior forming a hollow nozzle located at a distal end of said barrel and opening into the interior of said barrel;
a plunger slidably mounted in said barrel and forming a longitudinal cavity;
a needle holder slidably mounted in said longitudinal cavity of said plunger and having a lateral arm;
means defining a spiral channel extending along a proximal end portion of said barrel for engaging said lateral arm of said needle holder and retracting said needle holder within the barrel in response to relative rotational movement between the barrel and the needle holder; and
latching means on said barrel for latching and unlatching said needle holder at a distal end of said spiral channel, and comprising a longitudinal track on an outer surface of said barrel and a locking element slidably mounted on said track for reciprocating movement between a locking position at said distal end of said spiral channel and a non-locking position away from said distal end of said spiral channel.

24. A syringe assembly, comprising:
an elongated, generally cylindrical barrel having a hollow interior forming a hollow nozzle located at a distal end of said barrel and opening into the interior of said barrel;
a plunger slidably mounted in said barrel and forming a longitudinal cavity;
a needle holder slidably mounted in said longitudinal cavity of said plunger and having a lateral arm;
means defining a spiral channel extending along a proximal end portion of said barrel for engaging said lateral arm of said needle holder and retracting said needle holder within the barrel in response to relative rotational movement between the barrel and the needle holder; and
latching means on said barrel for latching and unlatching said needle holder at a distal end of said spiral channel, and comprising a locking element formed as an integral part of the outer surface of said barrel and including an integral hinge for permitting pivoting movement of said locking element between a locking position at said distal end of said spiral channel and a non-locking position spaced away from said distal end of said spiral channel.

25. A syringe assembly, comprising:
- an elongated, generally cylindrical barrel having a hollow interior forming a hollow nozzle located at a distal end of said barrel and opening into the interior of said barrel;
- a plunger slidably mounted in said barrel and forming a longitudinal cavity;
- a needle holder slidably mounted in said longitudinal cavity of said plunger;
- means defining a spiral channel extending along a proximal end portion of said barrel for engaging said needle holder and retracting said needle holder within the barrel in response to relative rotational movement between the barrel and the needle holder;
- wherein said needle holder includes a lateral arm for engaging the spiral channel and said barrel has an open end and said plunger includes recesses alignable with said open end of said barrel for defining a relief space for deformation of said open end of the barrel to permit initial insertion of said lateral arm of said needle holder past said open end of said barrel and into said spiral slot.

26. An over-the-needle catheter and syringe assembly, comprising:
- an elongated, generally cylindrical barrel having a hollow interior forming a hollow nozzle located at a distal end of said barrel and opening into the interior of said barrel;
- a plunger slidably mounted in said barrel and forming a longitudinal cavity;
- a needle holder slidably mounted in said longitudinal cavity of said plunger and having a lateral arm;
- means defining a spiral channel on said barrel extending along a proximal end portion of said barrel for engaging said lateral arm of said needle holder and retracting said needle holder within the barrel in response to relative rotational movement between the barrel and the needle holder;
- said barrel including means for strengthening said proximal end portion of said barrel;
- latching means on said barrel for latching and unlatching said needle holder at a distal end of said spiral channel;
- an over-the-needle catheter; and
- cooperating locking means on said catheter and said syringe for releasably securing said catheter to said syringe.

27. The catheter and syringe assembly of claim 26, wherein said cooperating locking means includes a luer taper located on said syringe which engages with a mating luer taper located on said catheter.

28. The catheter and syringe assembly of claim 26, said catheter further including a valve.

29. The catheter and syringe assembly of claim 28, wherein said valve comprises a slit valve.

30. The catheter and syringe assembly of claim 28, wherein said valve comprises a rotary ball valve.

31. The catheter and syringe assembly of claim 26, wherein said catheter comprises a catheter body, and an elongated, generally cylindrical catheter tip extending from said body.

32. The catheter and syringe assembly of claim 31, and further including a slit valve in said catheter body.

33. The catheter and syringe assembly of claim 26, wherein said catheter comprises a pair of orthogonally disposed catheter body portions, an elongated projecting catheter tip aligned with one of said body portions and a valve for operatively coupling said catheter body portions with said tip.

34. The catheter and syringe assembly of claim 33, wherein said valve comprises a rotary ball valve.

35. A syringe assembly, comprising:
- an elongated, generally cylindrical barrel having a hollow interior forming a hollow nozzle located at a distal end of said barrel and opening into the interior of said barrel;
- a plunger slidably mounted in said barrel and forming a longitudinal cavity;
- a needle holder slidably mounted in said longitudinal cavity of said plunger and having a lateral arm;
- means defining a spiral channel extending along a proximal end portion of said barrel for engaging said lateral arm of needle holder and retracting said needle holder within the barrel in response to relative rotational movement between the barrel and the needle holder; and
- latching means on said barrel for latching and unlatching said needle holder at a distal end of said spiral channel, and comprising a locking tab hingedly joined to said barrel and movable between a locking position in engagement with said lateral arm of said needle holder at said distal end of said spiral channel and a non-locking position out of engagement with said lateral arm of said needle holder.

* * * * *